United States Patent [19]

Russo

[11] Patent Number: 4,540,413
[45] Date of Patent: Sep. 10, 1985

[54] CARDIOPULMONARY DRAINAGE COLLECTOR WITH BLOOD TRANSFER ADAPTER

[76] Inventor: Ronald D. Russo, 8 Candleberry Rd., Barrington, R.I. 02806

[21] Appl. No.: 505,236

[22] Filed: Jun. 17, 1983

[51] Int. Cl.³ .............................................. A61M 1/00
[52] U.S. Cl. .................................................... 604/320
[58] Field of Search ............... 604/320, 321, 319, 317, 604/318

[56] References Cited
U.S. PATENT DOCUMENTS
3,750,692 8/1973 Tibbs ............................... 604/321 X Primary Examiner—William H. Grieb
Attorney, Agent, or Firm—Robert J. Doherty

[57] ABSTRACT

A drainage collector capable of draining and collecting fluid especially blood from the cardiopulmonary system during and after a surgical operation. A drainage sump is provided with a liquid seal to prevent outside air from entering the cardiopulmonary space. A dry suction control means with a built in positive pressure relief valve and high negative relief valve is incorporated within the drainage collector. Further, a blood transfer adapter is provided such that collected blood can be readily transferred to either a blood bag or to an autotransfusion device for recirculation of processed blood back into the patient.

16 Claims, 4 Drawing Figures

CARDIOPULMONARY DRAINAGE COLLECTOR WITH BLOOD TRANSFER ADAPTER

BACKGROUND OF THE INVENTION

This invention relates to a surgical drainage system and more particularly to a device designed to facilitate controlled removal of blood and recirculation of the patient's own blood if desired.

Surgeons go to great lengths to try to minimize the amount of blood loss during an operation on the heart, lungs, or internal aortic system since they must replace the patient's own blood with donored blood. Recent advances in technology and medicine have provided the ability to collect and recycle the patient's own previously lost blood (autotransfusion).

There are obvious advantages to the patient in autotransfusion; however, the apparatus and collection means are both complicated and expensive.

First, the level of suction must be controlled since excessive levels of suction tend to damage the blood cell structure. Next the blood must be collected in a rigid reservoir and then pumped into a blood bag for another transferal to a blood processor. From the processor the purified blood is then placed in a blood bag and reinfused intravenously into the patient.

After surgery, especially open heart surgery, there is continued leakage of blood into the pericardial space from sutured blood vessels, etc. Typically, surgeons place a large bore drain in the lower portion of the pericardial space and drain the blood into a collection bottle. Such post operatively collected blood can amount to anywhere between several hundred cubic centimeters to up to two liters. There is no present means for salvaging this blood such that it could also be recycled since post operative blood loss must also be replaced.

One of the main reasons for autotransfusing the patient's own blood is to eliminate the possibility of hepatitis infection from donored blood in a critical operation such as heart surgery. If donored blood must be used post operatively then the original surgical autotransfusion advantages are compromised and the patient is then subjected to undue risk and the potential for complications.

SUMMARY OF THE INVENTION

The present invention provides a cardiopulmonary collector device which overcomes the difficulties noted above. The present device can be used during the surgical procedure to collect blood and readily permit its transfer for blood processing. The device further includes means for controlling suction during the operation and both a positive pressure relief valve and a high negative pressure relief valve.

The collector device has a lower sump portion which provides a liquid seal to prevent air from post operatively entering the patient's cardiopulmonary space. Post operative bleeding is contained and a convenient simple transfer adapter is provided in the collector such that collected blood can be transferred for processing and reinfusion. Previously, this blood would be discarded and donored blood would be used as the replacement. In addition, means in the form of a convenient screw cap is provided such that an anti-coagulating solution such as heparin can be easily added to the collector to act as both the liquid seal and to also prevent blood clots from forming in the collector.

It is the primary object of the present invention to provide a device capable of controlling applied suction during a surgical operation to reduce cell damage to collected blood.

It is a further object of this invention to provide a convenient means for adding anti-coagulating fluid to the collector to prevent blood clots from forming in collected blood.

It is a further object of this invention to have the added anti-coagulating fluid further act as a liquid seal to prevent outside air from refluxing back up to the surgical site.

It is a further object of this invention to provide a convenient and aseptic transfer means for removing collected blood which can be reprocessed and autotransfused back to the patient.

It is a further object of the present invention to provide a means within the collector for relieving any positive pressure build up.

It is a further object of the present invention to provide a means for relieving any excessive negative pressure which may be applied to the collector.

Other objects and many of the advantages of the present invention will become apparent from the detailed description that follows with the accompanying drawings.

DESCRIPTION OF THE DRAWINGS

In the drawings which illustrate the best mode presently contemplated for carrying out the present invention.

DESCRIPTION OF THE PREFERRED EMBODIMENT

Figure 1:
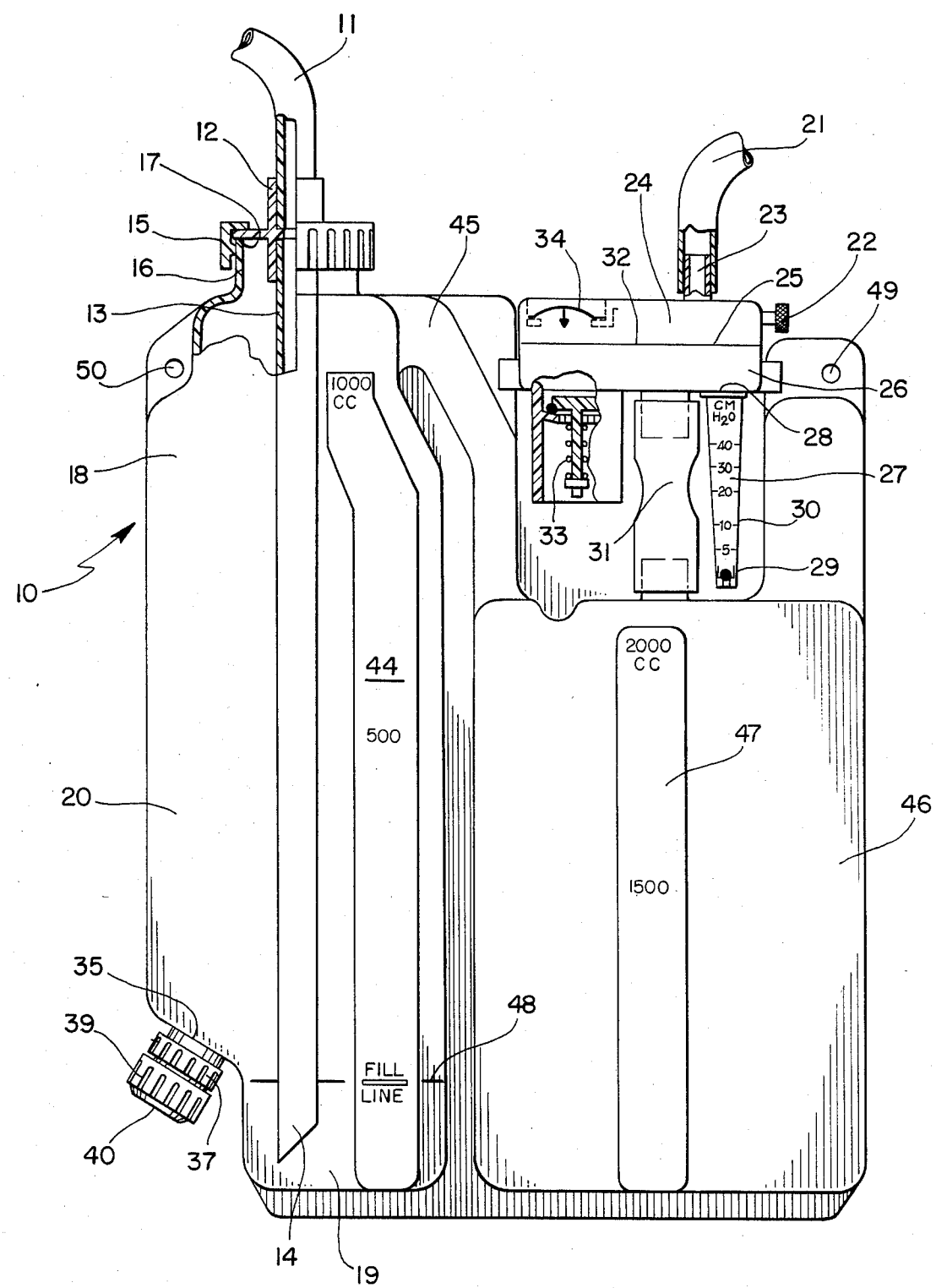
FIG. 1 is a front elevational view of the present invention with selected portions sectioned for clarity.
Figure 2:
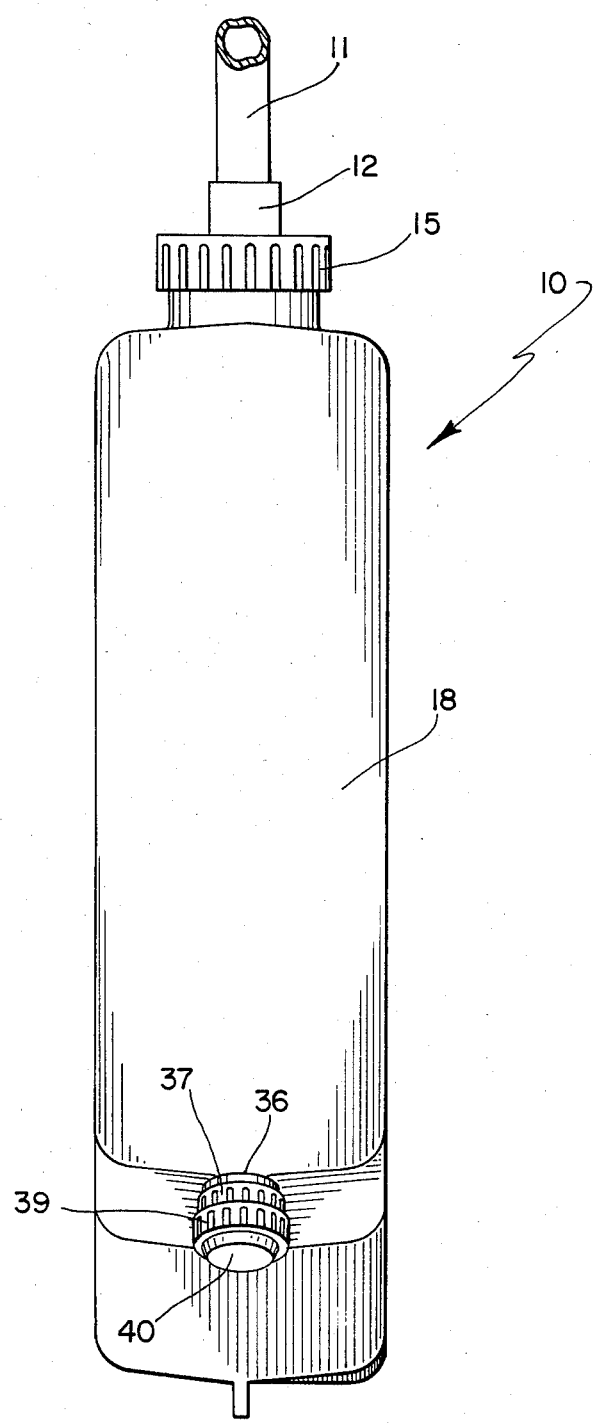
FIG. 2 is a left side view thereof.

Referring now to the drawings a cardio-pulmonary collector device 10 constructed in accordance with the present invention is shown. A pliable patient drainage tube 11 which drains the surgical site is solvent cemented or otherwise connected to a coupling 12 which is of a rigid plastic material, i.e., PVC. Also solvent cemented onto the bottom of the coupling is an extruded rigid plastic, i.e., PVC, drain tube 13 having a slanted end 14. A screw adapter 15 fits over coupling 12 and attaches the entire patient drainage tube system and coupling to a collector entry opening 16 which also has a mating screw thread. The coupling forms a compression seal at point 17 of the entry opening.

A collector container 18 is blow molded or otherwise formed from a rigid clear plastic such as PVC or PETG. Prior to the operation about 75 cc of anti-coagulating fluid is placed in the collector through an entry opening which falls into lower sump section 19 of first chamber 20. Aspirated blood during the operation is now suctioned into first chamber 20.

The collector is attached to a hospital suction source by a connecting tube 21. Suction is regulated by a thumb screw 22 which selectively opens or closes an orifice 23 in the suction line. The screw is housed in a control assembly housing or module 24 which is formed as by injection molding of upper and lower sections 25 and 26 respectively. Attached to the lower section 26 is suction indicator tube 27 which is molded of a clear plastic and glued or otherwise fastened in place as shown. The tube 27 includes an opening 28 at the top thereof. In the lower portion of the tube 27, a metal ball 29 is positioned. Both the tube 27 and ball 29 are calibrated to indicate applied suction as thumb screw 22 is adjusted. The ball will rise and indicate in cm $H_2O$ on the lettered face 30 of the tube 27. Suction is applied to the interior of the collector device via a connecting tube 31 formed of PVC or another suitable material. The control module is connected together as by solvent cement at joint 32.

At high negative suction relief valve 33 which is of the spring loaded poppet type is positioned in lower section 26. The valve is preset to relieve excessive amount of suction above, i.e., 60 cm $H_2O$, if an operator inadvertently applies excessive suction. A positive pressure relief valve 34 which is a silicone umbrella molded valve which will vent to atmosphere any build up of positive pressure above, i.e., 3 cm $H_2O$, is positioned in the upper section 25. Blood gases can build up within the collector and, accordingly, can be vented via valve 34. Collected blood can be readily removed by way of a transfer adapter 35 located above sump 19.

Figure 3:
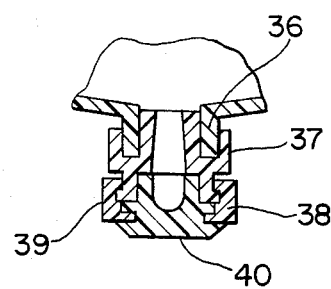
FIG. 3 is a sectional view showing the transfer adapter taken along line 3—3 of FIG. 1.

Now turning to FIG. 3, the construction of the three-part adapter 35 is shown. Solvent cemented or otherwise connected onto a stem 36 is a threaded adapter 37, e.g., is injection molded with screw threads. A cap 38 having a rigid injection molded portion 39 with puncturable seal 40 snapped into place is removably mounted onto adapter 37. The cap 38 becomes a removable two-part assembly. Blood collected in first chamber 20 can be readily removed by a blood transfer needle connecting tube (not shown) which punctures seal 40. This connecting tube will attach to a standard blood bag for collection of the transferred blood. Once in the blood bag the blood can be processed for reinfusion.

Figure 4:
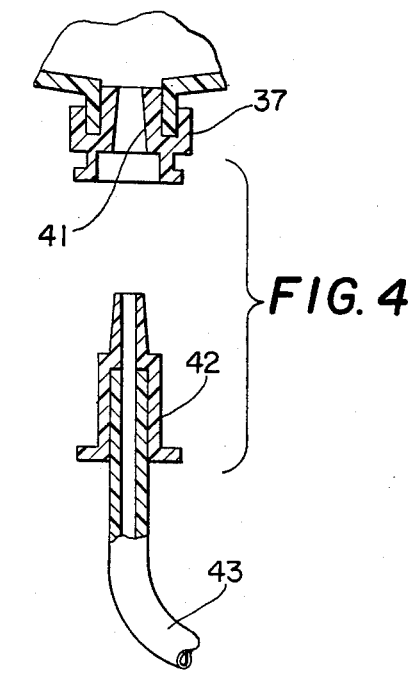
FIG. 4 is an exploded sectional view of the transfer adapter with its cap removed and further showing a blood transfer connector.

An alternate continual means of aseptically transferring collected blood is shown in FIG. 4 which shows cap 38 removed. The adapter 37 has an internal female luer fitting 41. This fitting will permit the ready connection of a male luer 42 which may be connected to a standard blood transfusion tubing line. This tubing line if connected directly to adapter 37 will permit the continual transferral of collected blood to a blood bag. This connection will further permit connection directly to an auto-transfusion processing machine. Screw cap 38 can be replaced at anytime.

Post operatively blood will continue to collect in first chamber 20. At anytime blood can be transferred through adapter 37. The first collection chamber 20 may have a capacity of 1000 cc as seen on scale 44. An overflow passageway 45 is integrally molded into the container 18 such that collected blood can overflow into second chamber 46 which provides an additional 1000 cc capacity as indicated on scale 47 for a total capacity of, e.g., 2000 cc.

The post operatively liquid seal level 48 in sump portion 19 provides a means for indicating air leakage from the pulmonary space and will provide a liquid seal preventing outside air from entering the patient tube 14. Hang holes 49, 50 are provided for hooks (not shown) for convenient attachment to bedside after the operation. Screw cap 15 can be opened for convenient emptying of the collector if desired.

Obviously many modifications or variations of the present invention are possible in light of the above teachings.

What is claimed is:

1. A drainage collector capable of draining and collecting body fluids from a patient especially blood from a surgical site, said collector comprising a closed collection chamber having first and second openings, said first opening adapted for attachment to a drainage tube from the surgical site, a sump provided within a lower portion of the chamber and adapted for receipt of said drainage tube, said sump providing a liquid seal to prevent reflux of air from entering said patient tube yet permitting air from the patient tube to escape into said chamber and wherein body fluids directed into said sump upwardly rise towards a downstream terminal portion of said chamber, an air passageway in the downstream terminal portion of said chamber permitting the escape of collected gases through said second opening, said second opening forming an exit from the chamber in air communication with said air passageway, dry means operatively associated with said exit for controlling suction applied to said chamber via said second opening, said chamber including a positive pressure relief valve, and said chamber further incorporating transfer means wherein collected body fluid can be aseptically transferred or emptied therefrom.

2. A drainage collector according to claim 1, wherein said means of controlling suction comprising an adjustable controller combined with a visual indicator to indicate the level of applied suction in direct response to the adjustable controller.

3. A drainage collector according to claim 1 including a high negative suction relief valve.

4. A drainage collector according to claim 3 wherein said positive pressure relief valve and said high negative suction relief valve are operatively associated with said second opening exit.

5. A drainage collector according to claim 1, said chamber comprising separate first and second chamber sections disposed side by side and interconnected by an overflow passage extending between the upper portions of said chamber sections, said liquid seal disposed in said first chamber section and said downstream terminal portion of said chamber being the upper portion of said second chamber section.

6. A drainage collector capable of draining and collecting body fluids from a patient especially blood from a surgical site, said collector comprising a closed collection chamber having first and second openings, said first opening in the upper portion thereof, a drainage tube adapted for connection to said first opening, said drainage tube further extending inside said chamber, the juncture between said drainage tube, said first opening in the collector, and the interior extending drainage tube forming an air tight seal, said interior extending drainage tube in fluid communication with the lower portion of the collector, means for adding fluid to the lower portion of said chamber to form a liquid seal between the interior drainage tube and the lower portion of the chamber, an upper portion of the collector acting as a passageway for escaped air from the interior drainage tube, said upper portion including said second opening in turn forming a chamber exit port adapted for connection to a suction control module for selectively controlling the level of applied suction to the collector, said suction control module comprising a variable dry controller in combination with a visual indicator to show the level of suction being applied in response to the variable action of the controller, an exit port on said suction module for connection to an external suction source, said control module including a positive pressure relief value, said collector further comprising a transfer means in the lower portion of said chamber wherein collected body fluid can be aseptically transferred or emptied therefrom, said transfer means positioned above the level of the liquid seal such that body fluids from the collector may be continuously drained from the collector down to the level of the liquid seal.

7. A drainage collector according to claim 6 wherein a high negative suction relief valve is provided in said control module.

8. A drainage collector according to claim 6 wherein the opening and patient tube juncture are connected by a removable screw coupling.

9. A drainage collector according to claim 6 wherein the transfer means comprises a puncturable seal.

10. A drainage collector according to claim 6 wherein the transfer means comprises a removable seal cap.

11. A drainage collector according to claim 6 wherein the collector comprises at least first and second chamber sections.

12. A drainage collector according to claim 11 with a first chamber section housing the liquid seal and a second overflow chamber section connected to the first chamber section.

13. A drainage collector according to claim 6 wherein the collector is a blow molded rigid container and the suction control module is a separate unit attached to the exit port of the blow molded container.

14. A drainage collector according to claim 6 wherein the suction control module further houses said positive pressure relief valve and a high negative suction relief valve.

15. A drainage collector according to claim 6 wherein means are provided on the collector for hanging the collector at bedside.

16. A drainage collector according to claim 6, said chamber comprising separate first and second chamber sections disposed side by side and interconnected by an overflow passage extending between the upper portions of said chamber sections, said liquid seal disposed in said first chamber section and said control module disposed above the upper portion of said section chamber section.

* * * * *